US012708753B2

(12) United States Patent
Calistri-Yeh et al.

(10) Patent No.: US 12,708,753 B2
(45) Date of Patent: Aug. 18, 2026

(54) MEDICAL TUBING AND FORMULATIONS THEREFOR

(71) Applicant: CareFusion 303, Inc., San Diego, CA (US)

(72) Inventors: Mildred Calistri-Yeh, San Diego, CA (US); Zehra Sevinc, San Diego, CA (US); Seth Strand, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 862 days.

(21) Appl. No.: 17/975,490

(22) Filed: Oct. 27, 2022

(65) Prior Publication Data

US 2023/0133021 A1 May 4, 2023

Related U.S. Application Data

(60) Provisional application No. 63/273,019, filed on Oct. 28, 2021.

(51) Int. Cl.
*A61M 39/08* (2006.01)
*A61L 29/08* (2006.01)
(Continued)

(52) U.S. Cl.
CPC ............ *A61M 39/08* (2013.01); *A61L 29/08* (2013.01); *A61L 29/14* (2013.01); *A61M 5/1413* (2013.01); *A61M 25/0045* (2013.01); *A61M 2025/0059* (2013.01); *A61M 2039/082* (2013.01); *A61M 2205/02* (2013.01)

(58) Field of Classification Search
CPC ................ A61M 39/08; A61M 5/1413; A61M 25/0045; A61M 2025/0059; A61M 2039/082; A61M 2205/02; A61L 29/08; A61L 29/14
See application file for complete search history.

(56) References Cited

U.S. PATENT DOCUMENTS 5,738,923 A 4/1998 Ko et al.
5,919,570 A * 7/1999 Hostettler ................ B05D 7/02 428/424.8

(Continued)

FOREIGN PATENT DOCUMENTS

EP 0265839 A2 5/1988
EP 0422632 A2 4/1991

(Continued)

OTHER PUBLICATIONS

International Preliminary Report on Patentability from the International Preliminary Examining Authority for Application No. PCT/US2022/047913, dated Sep. 7, 2023, 17 pages.

(Continued)

*Primary Examiner* — Cris L. Rodriguez
(74) *Attorney, Agent, or Firm* — MASCHOFF BRENNAN

(57) ABSTRACT

Medical tubing has at least one layer having a composition prepared from a melt blend of (i) a thermoplastic material, (ii) a filler and (iii) a heat reactive coupling agent. The medical tubing can have a kink resistance no worse than a medical tube composed of polyvinyl chloride with the same tubing wall dimensions. The medical tubing can be multi-layer and can include single lumen and multi-lumen tubing.

22 Claims, 3 Drawing Sheets

| Base: MD50278 Medalist SEBS/PP compound | | | | | | | |
|---|---|---|---|---|---|---|---|
| StdOrder | Run Order | CenterPt | Blocks | Filler Type | Filler Conc, wt% | Coupling Type | Coupling Conc, wt% |
| 4 | 1 | 1 | 1 | 325G Mica | 5 | L12/L | 0 |
| 1 | 2 | 1 | 1 | Spheriglass 5000 | 0.1 | L12/L | 0 |
| 2 | 3 | 1 | 1 | 325G Mica | 0.1 | L12/L | 5 |
| 7 | 4 | 1 | 1 | Spheriglass 5000 | 5 | NZ 12/L | 0 |
| 9 | 5 | 0 | 1 | Spheriglass 5000 | 2.55 | L12/L | 2.5 |
| 11 | 6 | 0 | 1 | Spheriglass 5000 | 2.55 | NZ 12/L | 2.5 |
| 3 | 7 | 1 | 1 | Spheriglass 5000 | 5 | L12/L | 5 |
| 6 | 8 | 1 | 1 | 325G Mica | 0.1 | NZ 12/L | 0 |
| 5 | 9 | 1 | 1 | Spheriglass 5000 | 0.1 | NZ 12/L | 5 |
| 10 | 10 | 0 | 1 | 325G Mica | 2.55 | L12/L | 2.5 |
| 8 | 11 | 1 | 1 | 325G Mica | 5 | NZ 12/L | 5 |
| 12 | 12 | 0 | 1 | 325G Mica | 2.55 | NZ 12/L | 2.5 |
| CONTROL | 13 | Ref | Ref | None | 0 | None | 0 |

(51) Int. Cl.

| | |
|---|---|
| ***A61L 29/14*** | (2006.01) |
| ***A61M 5/14*** | (2006.01) |
| ***A61M 25/00*** | (2006.01) |

(56) References Cited

U.S. PATENT DOCUMENTS

| | | | | |
|---|---|---|---|---|
| 6,187,400 | B1 | 2/2001 | Woo et al. | |
| 6,994,913 | B1 * | 2/2006 | Niki | C08G 18/4854 428/394 |
| 7,387,826 | B2 * | 6/2008 | Burgmeier | F16L 11/12 428/36.9 |
| 8,137,083 | B2 | 3/2012 | Zhou | |
| 8,735,491 | B2 * | 5/2014 | Kim | A61M 39/08 604/533 |
| 9,670,392 | B2 | 6/2017 | Larson et al. | |
| 9,708,517 | B2 | 7/2017 | Mennecke et al. | |
| 9,738,781 | B2 * | 8/2017 | Zhou | C08L 53/00 |
| 2001/0033924 | A1 * | 10/2001 | Qian | C08K 9/08 428/297.1 |
| 2002/0090476 | A1 * | 7/2002 | Ling | B32B 27/32 428/36.91 |
| 2003/0044555 | A1 | 3/2003 | Ding et al. | |
| 2006/0055077 | A1 * | 3/2006 | Heikkila | C08K 3/08 264/173.16 |
| 2007/0128393 | A1 * | 6/2007 | Moulton | B29C 66/43121 428/36.9 |
| 2009/0127801 | A1 * | 5/2009 | Heikkila | A01K 95/005 168/4 |
| 2010/0280164 | A1 * | 11/2010 | Heikkila | B60C 1/00 524/493 |
| 2011/0236699 | A1 * | 9/2011 | Heikkila | C08K 5/0091 524/394 |
| 2011/0319837 | A1 * | 12/2011 | Uehara | B32B 27/34 138/177 |
| 2014/0079898 | A1 * | 3/2014 | Kaushik | C08L 67/025 524/359 |
| 2018/0086905 | A1 * | 3/2018 | Zhang | A61L 27/16 |
| 2019/0054214 | A1 | 2/2019 | Hermel-Davidock et al. | |
| 2019/0346072 | A1 * | 11/2019 | Gopalan | B32B 5/02 |
| 2020/0271246 | A1 * | 8/2020 | Manas-Zloczower | F16L 11/088 |
| 2021/0382211 | A1 * | 12/2021 | Heikkila | E01F 9/524 |

FOREIGN PATENT DOCUMENTS

| | | | | |
|---|---|---|---|---|
| EP | 0926201 | A1 | 6/1999 | |
| EP | 2358806 | B1 | 10/2015 | |
| EP | 2261278 | B1 | 2/2019 | |
| GB | 2238962 | A | 6/1991 | |
| WO | WO-2007139199 | A1 * | 12/2007 | C08L 53/025 |
| WO | WO-2009143251 | A2 | 11/2009 | |
| WO | WO-2017040782 | A1 | 3/2017 | |

OTHER PUBLICATIONS

Written Opinion from the International Preliminary Examining Authority for Application No. PCT/US2022/047913, dated May 31, 2023, 9 pages.

Monte, Making Nanotechnology Work with Titanates and Zirconates, dated 2005, 21 pages.

Pritchard, Plastics Additives, dated Mar. 1, 2005, 207 pages.

Titanates and Zirconates in Thermoplastic and Elastomer Compounds, dated 2018, 12 pages, https://4kenrich.com/technical-information/titanates-and-zirconates-in-thermoplastic-and-elastomer-compounds/.

International Search Report and Written Opinion of the International Search Authority for Application No. PCT/US2022/047913, dated Feb. 20, 2023, 13 pages.

European Office Action for Application No. 22812965.6, dated Mar. 19, 2026, 8 pages.

* cited by examiner

| Base: MD50278 Medalist SEBS/PP compound | | | | | | | |
|---|---|---|---|---|---|---|---|
| StdOrder | Run Order | CenterPt | Blocks | Filler Type | Filler Conc, wt% | Coupling Type | Coupling Conc, wt% |
| 4 | 1 | 1 | 1 | 325G Mica | 5 | L12/L | 0 |
| 1 | 2 | 1 | 1 | Spheriglass 5000 | 0.1 | L12/L | 0 |
| 2 | 3 | 1 | 1 | 325G Mica | 0.1 | L12/L | 5 |
| 7 | 4 | 1 | 1 | Spheriglass 5000 | 5 | NZ 12/L | 0 |
| 9 | 5 | 0 | 1 | Spheriglass 5000 | 2.55 | L12/L | 2.5 |
| 11 | 6 | 0 | 1 | Spheriglass 5000 | 2.55 | NZ 12/L | 2.5 |
| 3 | 7 | 1 | 1 | Spheriglass 5000 | 5 | L12/L | 5 |
| 6 | 8 | 1 | 1 | 325G Mica | 0.1 | NZ 12/L | 0 |
| 5 | 9 | 1 | 1 | Spheriglass 5000 | 0.1 | NZ 12/L | 5 |
| 10 | 10 | 0 | 1 | 325G Mica | 2.55 | L12/L | 2.5 |
| 8 | 11 | 1 | 1 | 325G Mica | 5 | NZ 12/L | 5 |
| 12 | 12 | 0 | 1 | 325G Mica | 2.55 | NZ 12/L | 2.5 |
| CONTROL | 13 | Ref | Ref | None | 0 | None | 0 |

FIG. 1

MEDICAL TUBING AND FORMULATIONS THEREFOR

CROSS-REFERENCE TO RELATED APPLICATIONS

This application claims priority to U.S. Provisional Application Nos. 63/273,019, filed Oct. 28, 2021, the disclosure of which is incorporated by reference herein in its entirety.

TECHNICAL FIELD

The present disclosure generally relates to medical tubing and, in particular, to flexible medical tubing having kink resistance that can be prepared from thermoplastic materials, fillers and reactive coupling agents and preferably without polyvinyl chloride or plasticizers. Such tubing can be used for medical devices such as tubing for administration of medical fluid by infusion, as tubing for extension sets, catheters, etc., including those with complex tubing configurations with multiple lumens.

BACKGROUND

Plastic tubing is extensively used in the medical field, particularly for patient analysis and treatment procedures. Such uses require the tubing to be flexible, easy to pinch and rebound quickly. Soft tubing such as polyvinyl chloride with plasticizer have been used in infusion sets for many years. Unfortunately, plasticized polymeric materials such as plasticized polyvinyl chloride can be sticky and can lead to occlusion and tearing of the tubing. In addition, tubing made with plasticizers have the potential to migrate into and contaminate fluid transported through the tubing.

However, a continuing need exists to prepare medical tubing such as for delivery of medicinal fluids.

SUMMARY OF THE DISCLOSURE

Aspects of the subject technology relate to medical tubing and, in particular, to medical tubing for administration of medical fluid by infusion and to medical tubing for use as extension sets and catheters. In accordance with certain aspects, medical tubing can comprise one or more layers having a composition prepared from a melt blend of (i) a thermoplastic material, (ii) a filler (e.g., an inorganic filler and/or a non-silane reactive filler) and a heat reactive coupling agent. Other layers of the tubing can include an inner layer in contact with medicinal fluid such as a polyolefin, e.g., a polyethylene, with the melt blended composition forming an outer layer. Further, medical tubing of the present disclosure can include single lumen tubing and tubing having more than one lumen, i.e., multi-lumen medical tubing.

Advantageously, the medical tubing or a layer thereof of the present disclosure can be substantially free of a plasticizer or free of polyvinyl chloride but still have kink resistance. In some aspects, the medical tubing has a kink resistance sufficient to perform with pumps and preferably comparable to medical tube composed of polyvinyl chloride with the same wall dimensions.

The subject technology also relates to an infusion set comprising the medical tubing. The subject technology also relates to preparing a melt blend of the composition that can be used to form the medical tubing or layer thereof. In an aspect, the medical tubing can be prepared by compounding the thermoplastic material, non-silane reactive filler and heat reactive coupling agent with sufficient heat to form the melt blended composition. The formed melt blended composition can be pelletized or extruded into an appropriate form for storage or transporting, or the formed melt blended composition can be extruded directly, or in a subsequent step, to the medical tubing.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawing, which is included to provide further understanding and is incorporated in and constitute a part of this specification, illustrate disclosed embodiments and together with the description serve to explain the principles of the disclosed embodiments. In the drawings:

FIG. 1 is a table of several formulations prepared by mixing a thermoplastic elastomer (SEBS/PP), filler and coupling agent. The table also includes a control formulation.

DETAILED DESCRIPTION OF THE DISCLOSURE

Figure 2:
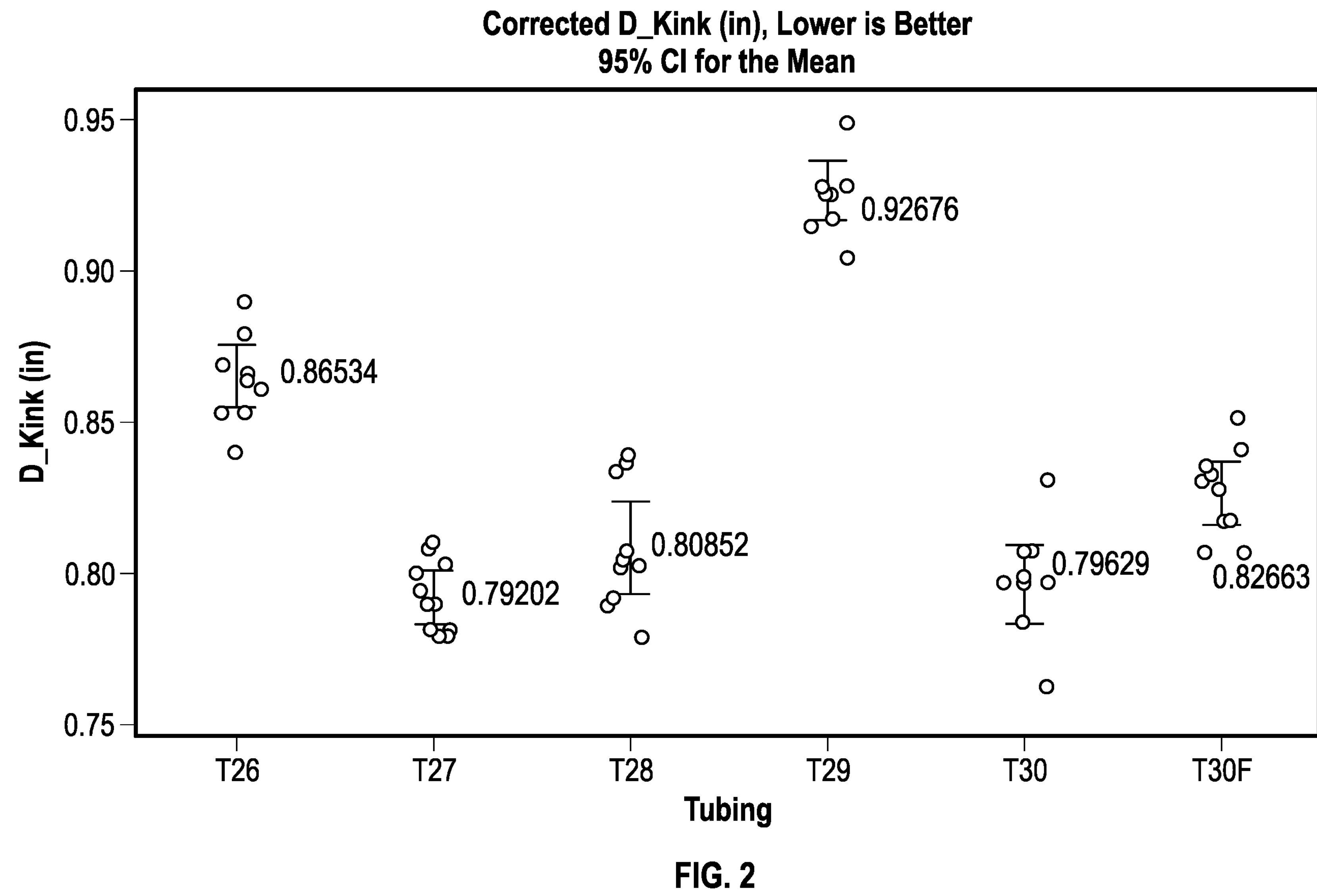
FIG. 2 is a plot of corrected kink results for typical PVC tubing.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to medical tubing and, in particular, to medical tubing for administration of medical fluid by infusion and to medical tubing for use as single-lumen or multiple-lumen extension tubing and catheters. In accordance with certain aspects, medical tubing can comprises at least one layer having a composition prepared from a melt blend of (i) a thermoplastic material, (ii) a non-silane reactive filler and a heat reactive coupling. Further, medical tubing of the present disclosure can include single lumen tubing and tubing having more than one lumen, i.e., multi-lumen medical tubing. Advantageously, the medical tubing of the present disclosure has sufficient kink resistance for use with infusion pumps. Other layers of the tubing can include an inner layer in contact with medicinal fluid such as a polyolefin, e.g., a polyethylene, with the melt blended composition forming an outer layer. In some aspects, the medical tubing has a kink resistance sufficient to perform with pumps and preferably comparable to medical tube composed of polyvinyl chloride with the same wall dimensions. In some aspects, medical tubing of the present disclosure can have a range of wall thickness from about 0.0075 inches to about 0.03 inches, e.g., a wall thickness of about 0.01 to about 0.025 inches, and a kink resistance in a range of from about 0.70 inches to about 1.1 inches, such as from about 0.89 inches to about 0.95 inches.

It is believed the inorganic filler binds to the thermoplastic polymer chains through the heat reacted coupling agents forming a more or less unified polymer system that acts like a crosslinked material. Such a structure is expected to improve rebound properties of the thermoplastic polymeric material and elevate the kink resistance and pump ability under cyclic deformation.

Achieving a desired kink resistance and retaining the flow rate accuracy through typical pumping periods is difficult to achieve by any materials. The material is expected to have good retention of elastic properties, kink resistance, etc. through cycling during pump use. Kink resistance also requires a good balance of viscous and elastic properties of the polymer. PVC-free thermoplastic polyolefins (TPO) or thermoplastic elastomers (TPE) are more environmental friendly than PVC in the sense that such thermoplastics often do not include plasticizers or, to the extend they do so, at significantly lower quantities than typical PVC formulations required for tubing used with pump applications. Consequently leachable components from such thermoplastics can be minimized or eliminated. However, it has been difficult to match the viscoelastic properties of PVC or its tailorability with alternative materials while still meeting other desirable properties of PVC tubing such as solvent bonding, sterilizability, etc.

Some of the advantages of the compositions for the medical tubing of the present disclosure relative to PVC include one or more of relative cost comparability or less, environmentally friendly materials, lowered leachables, comparable or better flow rate and accuracy in pumping, pump and clamp compatibility, comparable or better kink resistance, superior tear resistance and less prone to bulging under fluid pressure, superior in compression set, hence rebound needed for clamp compatibility, simpler processing steps and reduced cycle times, useful for light sensitive medication delivery applications due to light blocking property of filler, and/or increased heat resistance.

In accordance with certain aspects, tubing for administration of intravenous can comprise polyvinyl chloride (PVC)-free thermoplastic polymeric materials. Such thermoplastic polymeric materials include, for example, one or more of, or a blend including, a thermoplastic olefin (TPO), such as polypropylene, polyethylene, a thermoplastic elastomer (TPE) such as a styrene-containing thermoplastic elastomer (S-TPE), such as a styrenic blocking copolymer (SBC), e.g., styrene-butadiene styrene copolymer (SBS), styrene-butadiene-styrene-styrene block copolymer (SBSS), styrene-isoprene-styrene (SIS), a polyolefin elastomer (POE). To improve thermo-oxidative and UV stability, an unsaturated rubber block of a S-TPE elastomer (e.g., the polybutadiene or polyisoprene rubber block of an SBS, SB SS or SIS polymer) can be hydrogenated to form hydrogenated styrene-based thermoplastic elastomers, which include, without limitation, styrene-ethylene-butylene-styrene thermoplastic elastomer (SEBS), styrene-ethylene/propylene-styrene (SEPS). High performance thermoplastic elastomer (TPE) has been designed as a sustainable alternative to flexible PVC for medical tubing and film. In addition, the tubing can include a blend of the hydrogenated styrene-based thermoplastic elastomer with a hydrogenated or saturated polyolefin such as polypropylene, e.g., homo, block and/or random polypropylene such as random copolymer polypropylene (RCPP), etc.

The thermoplastic material can be included as part of the tubing composition or in a layer composition in an amount from at least about 1 wt % to about 99 wt % based on the total weight composition of the medical tubing or the total weight composition of a layer of the tubing.

Useful fillers that can be included in the medical tubing or layer thereof include an inorganic filler and/or a non-silane reactive filler, e.g., silica, glass beads, metal carbonates such as calcium carbonate, metal oxides, carbon black, mica, nepheline syenite, etc. Such fillers can interact with the heat reactive coupling agent. Heat reactive coupling agent chemically bridge non-silane reactive fillers such as $CaCO_3$, carbon black—and silica, metal oxides, etc. with polymers. More specifically, muscovite mica, nepheline syenite, calcium carbonate and glass beads can also be used as fillers in the present formulations. As an example, mica and glass beads with particle sizes ranging from about 5 to about 26 micrometers can be used. The filler can be included as part of the tubing composition or in a layer composition in an amount from at least about 0.1 wt % to about 20 wt % based on the total weight composition of the medical tubing or the total weight composition of a layer of the tubing. For example, the composition can include the filler from about 0.1 wt %, such as at least about 0.5 wt %, 0.75% wt %, 1 wt %, but no more than about 20 wt %, such as no more than about 15 wt %, 10 wt %, 5 wt %, 3 wt %, 2 wt %, e.g. from about 1% to about 10 wt % of the total composition.

Heat reactive coupling agents that can be used with the medical tubing of the present disclosure include neopentyl (diallyl)oxy, tri(dioctyl)phosphato zirconate, neopentyl(diallyl)oxy, tri(dioctyl)phosphate titanate (available from Kenrich Petrochemicals, Inc.), KA® 301 Di-isobutyl(oleyl) aceto acetyl aluminate, KA 322 Di-isopropyl(oleyl)aceto acetyl aluminate, KR® OPPR Titanium IV bis octanolato, cyclo(dioctyl)pyrophosphato-O, O, KR OPP2 Titanium IV bis cyclo(dioctyl)pyrophosphato-O, O, KZ® TPP Zirconium IV 2-ethyl, 2-propenolatomethyl 1,3-propanediolato, cyclo di 2,2-(bis 2-propenolatomethyl) butanolato pyrophosphato-O, O, KZ® OPPR Zirconium IV bis 2-ethylhexanolato, cyclo(di 2-ethylhexyl)pyrophosphate, isopropyl triisostearoyl titanate, etc. Such heat reactive coupling agents can improve toughness, elongation, polymer flow at lower temperatures, thus resulting in faster extrusion, blow and injection mold cycle times and better-quality parts as measured by appearance, chemical resistance, impact resistance. In contrary, organo-silanes are non-functional as bonding agents since they have little or none reported surface interactions with calcium carbonate, barium, and boron, etc. Differently, heat reactive coupling agents such as disclosed here are more reactive than silane. Moreover, silanes react with water, rendering them difficult to handle in moist environments, and controlling quality through storage.

The heat reactive coupling agent can be included as part of the tubing composition or in a layer composition in an amount from at least about 0.5 wt % to about 20 wt % based on the total composition of the medical tubing or a composition of a layer of the tubing. For example the tubing composition can include the coupling agent from about 0.5 wt %, such as at least about 0.75% wt %, 1 wt %, but no more than about 20 wt %, such as no more than about 15 wt %, 10 wt %, 5 wt %, 3 wt %, 2 wt %, e.g. about 1% to about 10 wt % of the total composition of the tubing or a composition of a layer of the tubing.

The filler and heat reactive coupling agent can be adjusted to adjust to balance rigidity, processability, clarity of the material and performance. As the filler concentration increases in the tubing composition or layer thereof, the composition tends to lose transparency and gain the color of particular filler(s).

The medical tubing of the present disclosure can include additives in one or more layers thereof such as a colorant, UV blocker, radiopaque stripes, among other additives. Such additives can be in a main layer or an outer layer of the tubing.

In certain aspects of the subject technology, the medical tubing of the present disclosure can be substantially free of a plasticizer or free of polyvinyl chloride but still has kink resistance. Substantially free of PVC from a medical tube or layer thereof means PVC of less than about 0.1 wt % of the composition of the layer or tube.

A plasticizer is an additive that increase the plasticity or decrease the viscosity of a material, e.g., a polymeric material. As used herein a plasticizer is an additive that can be included in a polymeric material to increases the flexibility and reduces the harness of the polymeric material. Such plasticizers include, without limitation, low molecular weight esters including, aliphatic esters and aromatic esters, citrates, dibenzoates, gluterates, azelates, terephthalates, trialkyl-trimellitates. Aliphatic esters include, for example, sebacates, adipates such as di(2-ethylhexyl) adipate (DEHA), di(2-ethylhexyl azelate (DOZ), di (2-ethylhexyl sebacate (DOS). citrates such as acetyl tri-n-butyl citrate (ATBC) and n-butyryl-tri-n-hexyl citrate (BTHC), Acetyl tri-n-hexyl Citrae (ATHC) 1,2-cyclohexane dicarboxylic acid diisononyl ester (DINCH), etc. Aromatic esters include, for example, terephthalates, such as di(2-ethylhexyl) terephthalate (DEHT), phthalates, such as di(2-ethylhexyl) phthalate (DEHP), diisononyl phthalate (DINP), bis(2-propylheptyl phthalate (DPHP), diisodecyl phthalate (DIDP), tri-2-ethylhexyl Trimellitate(TOTM). Such plasticizers are preferably substantially excluded, if not entirely excluded, from the medical tubing or layer thereof of the present disclosure. Substantially excluded from a medical tube or layer thereof means less than about 0.1 wt % of the composition of the layer or tube.

The medical tubing of the present disclosure can have good solvent bondability. An indication of such bondability is swelling of the tubing in a given solvent that can be used to solvent bond the tubing to a part or other tube.

Tubing of the present disclosure is particularly useful with intravenous assemblies, gravity containers and/or infusion pumps for the transport of intravenous fluid to a patient. An assembly of tubing, valves, fittings, and needles that connect a fluid container to a patient intravenously may be referred to as an "IV set".

Infusion pumps are medical devices that may be used to administer intravenous (IV) fluids. An infusion pump can facilitate the delivery of IV fluids while controlling the volumes and rates for the delivery of such IV fluids. Some infusion pumps move fluid through tubing using a peristaltic pumping mechanism which compresses and releases flexible tubing to force fluid to move through the tube. For use in applications including IV sets and/or infusion pumps, tubing of the present discloser can have an inner diameter for flow of fluid therethrough ranging from about 1.5 mm to about 6 mm, e.g., from 2 mm to 4 mm and an overall sidewall thickness ranging from 0.2 mm to 0.8 mm, such as from 0.4 mm to 0.6 mm.

The subject technology also relates to preparing a melt blend of the composition that can be used to form the medical tubing or layer thereof. In an aspect, the medical tubing can be prepared by compounding (i) a thermoplastic material, (ii) a non-silane reactive filler and (iii) a heat reactive coupling with sufficient heat to form a melt blended composition. Such a melt blended composition can be prepared by an extruder, e.g., a twin screw extruder. The formed melt blended composition can be extruded directly to the medical tubing. Alternatively, the formed melt blended composition can be pelletized or extruded into an appropriate form for storage or transporting. The extruded pellets or other form can then be subsequently extruded into medical tubing.

For example, the thermoplastic polymeric material, filler and heat reactive coupling agent can be mixed in a twin screw extruder to form a compounded tubing composition which can then be extruded directly into tubing or pelletize with subsequent processing into tubing such as with a single screw extruder.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Several formulations were prepared by mixing the following components: a thermoplastic elastomer (SEBS/PP), filler and coupling agent. The thermoplastic materials with fillers and coupling agents, e.g., formulations, are shown in the table of FIG. 1. The table also includes a control formulation. The formulations were then melt blended by compounding in a twin screw extruder in the form of pellets and the pellets were subsequently extruded by a single screw extruder into medical tubing having an outer diameter of about 0.145 inches and inner diameter of about 0.107 inches. The extruded medical tubing was then tested with solvents to determine their swellability. Swelling studies indicated that the extruded tubing swelled in dibromomethane, cyclohexanone, ethylene dichloride. Swelling within the solvents suitable for medical devices is desired for solvent bonding compatibility. The materials not swelling would need alternate bonding techniques.

In addition, swelling of the extruded tubing formulations with fillers increased over control without fillers. That suggest increased diffusion of solvent into the thermoplastic material and potentially increasing the solvent bonding of the material. The swelling of the extruded tubing formulations with fillers increased over control without fillers was not expected.

This was unexpected because it was not expected that the fillers could increase adhesion or interact with the selected organic solvents. Fillers are inert and are known to be chemical resistant. Calcium carbonate ($CaCO_3$), for example, can be dissolved with strong acids while Mica, like all silicates, can be slowly dissolved by hot concentrated alkali. Otherwise, such fillers are not known to interact with organic solvents such as ethanol. Thus, swelling within chosen organic solvents and without heating, and detecting that change regardless of small % of filler present in the polymer were all surprising.

The extruded tubing was subjected to kink analysis. The kink analysis was conducted by the standard of EN13868. (Test methods for kinking of single lumen catheters and medical tubing—This Standard specifies test methods for kinking properties for single lumen catheters and medical tubing as they relate to the device ready for clinical use. The purpose of the standard is to ensure uniformity in the evaluation of tubing kink properties.) Corrected kink results are provided in FIG. 2 for typical PVC tubing as set out in the figure. FIG. 3 shows a plot of corrected kink distance in inches versus calculated wall thickness for several of extruded medical tubing with the formulations of the table in FIG. 1. Also shown in FIG. 3 is a triangle for kink distance values of control thermoplastic material without filler and coupling agent.

Even though results indicate the tubing design impacts corrected kink distance of the tubing, the formulations having the TPE together with filler and coupling agent show result in corrected kink distance similar to PVC.

Figure 3:
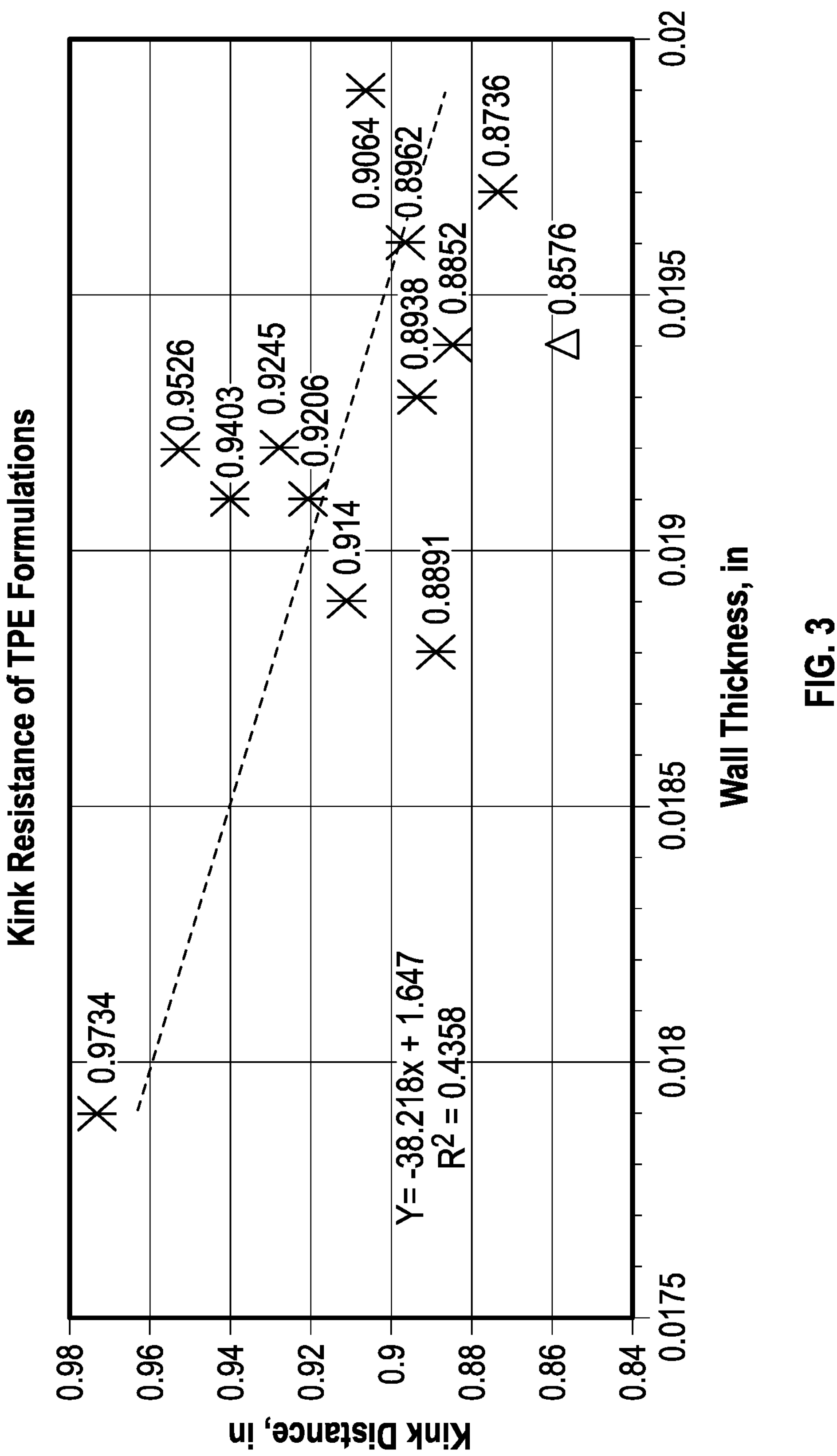
FIG. 3 is shows kink and dimensional data of formulated thermoplastic material according to aspects of the present disclosure relative to the thermoplastic material without filler and coupling agent.

For the tubing dimensions of 0.145" OD×0.019" wall thickness (WT), we measure 0.86" to 0.97" for kink resistance of TPE while competitive PVC tubing results in 0.79 to 0.93" (FIG. 2). FIG. 3 shows the impact of the wall thickness, hence the TPE tubing at 0.0190+/−0.002" target wall thickness provides a range of 0.89" to 0.95" kink resistance, that provides similar kink property to PVC tubing formulations within the measurement errors.

The extruded tubing was further subjected to e-beam radiation and preliminary results showed good e-beam radiation stability for the extruded tubing.

It is a major challenge to identify thermoplastic materials that can solvent bond comparable to PVC and simultaneously provide kink resistance comparable to PVC. The data shared in FIG. 3 indicates that TPE formulations disclosed here are comparable to PVC regarding kink resistance property within the expected measurement error of the test method. The swelling data indicated that the specific formulation attributes render improved adhesion property of the TPE over the TPE with no such additives in use.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for"

or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A medical tubing comprising:

an inner layer having a polyolefin; and an outer layer having a composition prepared from a melt blend of (i) a thermoplastic material including one or more of a thermoplastic olefin or a thermoplastic elastomer, or a blend thereof, (ii) a non-silane reactive filler and (iii) a heat reactive coupling agent, wherein the heat reactive coupling agent couples the non-silane reactive filler to the thermoplastic material, wherein the outer layer is at least one of: substantially free of polyvinyl chloride or substantially free of plasticizer.

2. The medical tubing of claim 1, wherein the outer layer is substantially free of polyvinyl chloride.

3. The medical tubing of claim 1, wherein the thermoplastic material includes the thermoplastic elastomer.

4. The medical tubing of claim 1, wherein the thermoplastic material comprises from 1 wt % to about 99 wt % of the composition based on the total weight of the composition.

5. The medical tubing of claim 1, wherein the filler comprises one or more of silica, glass beads, or metal carbonates.

6. The medical tubing of claim 1, wherein the filler comprises from 0.1 wt % to about 5 wt % of the composition based on the total weight of the composition.

7. The medical tubing of claim 1, wherein the heat reactive coupling agent comprises one or more of neopentyl (diallyl)oxy, tri (dioctyl)phosphato zirconate, neopentyl(diallyl) oxy, tri (dioctyl)phosphate titanate.

8. The medical tubing of claim 1, wherein the heat reactive coupling agent comprises from 0.5 wt % to about 20 wt % of the composition based on the total weight of the composition.

9. The medical tubing of claim 1, wherein the medical tubing has a wall thickness of about 0.01 to about 0.025 inches, and a kink resistance in a range of from about 0.70 inches to about 1.1 inches.

10. The medical tubing of claim 1, wherein the medical tubing can undergo solvent bonding.

11. An infusion set comprising the medical tubing of claim 10 bound to a medical connector.

12. The medical tubing of claim 1, wherein the medical tubing includes more than one lumen.

13. The medical tubing of claim 1, wherein the filler comprises one or more of calcium carbonate, metal oxides, carbon black, mica, or nepheline syenite.

14. The medical tubing of claim 1, wherein the filler includes mica having a particle size of about 5 micrometers to about 26 micrometers.

15. The medical tubing of claim 1, wherein the filler includes glass beads having a particle size of about 5 micrometers to about 26 micrometers.

16. The medical tubing of claim 1, wherein the thermoplastic material includes the thermoplastic elastomer and the thermoplastic elastomer is a styrene-based thermoplastic elastomer.

17. The medical tubing of claim 1, wherein the thermoplastic material includes the thermoplastic elastomer and the thermoplastic elastomer is a hydrogenated styrene-based thermoplastic elastomer.

18. The medical tubing of claim 1, wherein the outer layer is substantially free of plasticizer.

19. The medical tubing of claim 1, wherein the polyolefin includes polyethylene.

20. The medical tubing of claim 1, further comprising one or more additives including at least one of a colorant, a UV blocker, or radiopaque stripes.

21. The medical tubing of claim 20, wherein at least one of the one or more additives are included in the outer layer.

22. The medical tubing of claim 1, wherein the heat reactive coupling agent couples the non-silane reactive filler to the thermoplastic material by binding the non-silane reactive filler to thermoplastic polymer chains in the thermoplastic material.

* * * * *